United States Patent
Zhen et al.

(10) Patent No.: US 10,959,611 B2
(45) Date of Patent: Mar. 30, 2021

(54) VISUAL FIELD TESTING METHOD, SYSTEM, AND TESTING APPARATUS BASED ON HEAD-MOUNTED TESTING EQUIPMENT

(71) Applicant: ZHUHAI WIIFINE MEDINFORMATION TECHNOLOGY CO., LTD., Zhuhai (CN)

(72) Inventors: Yi Zhen, Beijing (CN); Weihong Zheng, Beijing (CN); Cong Zhang, Beijing (CN)

(73) Assignee: ZHUHAI WIIFINE MEDINFORMATION TECHNOLOGY CO., LTD., Zhuhai (CN)

( * ) Notice: Subject to any disclaimer, the term of this patent is extended or adjusted under 35 U.S.C. 154(b) by 0 days.

(21) Appl. No.: 16/633,573

(22) PCT Filed: Jun. 1, 2018

(86) PCT No.: PCT/CN2018/089606
§ 371 (c)(1),
(2) Date: Jan. 23, 2020

(87) PCT Pub. No.: WO2019/019805
PCT Pub. Date: Jan. 31, 2019

(65) Prior Publication Data
US 2020/0214552 A1    Jul. 9, 2020

(30) Foreign Application Priority Data
Jul. 26, 2017 (CN) .......................... 201710614917.4

(51) Int. Cl.
*A61B 3/024*    (2006.01)
*A61B 3/00*    (2006.01)
(Continued)

(52) U.S. Cl.
CPC .............. *A61B 3/024* (2013.01); *A61B 3/005* (2013.01); *A61B 3/0091* (2013.01); *A61B 3/113* (2013.01);
(Continued)

(58) Field of Classification Search
CPC ....... A61B 3/024; A61B 3/005; A61B 3/0091; A61B 3/113; A61B 2090/502; H04B 1/385; H04B 2001/3866; G06F 3/013
(Continued)

(56) References Cited

U.S. PATENT DOCUMENTS

| 5,956,124 A | 9/1999 | Dan |
| 2007/0013868 A1* | 1/2007 | Pugach .................. A61B 3/113 351/209 |

FOREIGN PATENT DOCUMENTS

| CN | 101018501 A | 8/2007 |
| CN | 101185016 A | 5/2008 |

(Continued)

OTHER PUBLICATIONS

State Intellectual Property Office of the P.R. China (ISA/CN), International Search Report for International Application PCT/CN2018/089606, dated Aug. 29, 2018, 2 pages.
(Continued)

*Primary Examiner* — Mohammed A Hasan
(74) *Attorney, Agent, or Firm* — MagStone Law LLP (57) ABSTRACT

The present disclosure relates to a visual field testing method, system, and testing apparatus based on head-mounted testing equipment. The method includes: transmitting, by the testing apparatus in electronic equipment, a start notification for starting monitoring of a movement trajectory of a pupil of a current eye to be tested to an eye movement tracking system after receiving a start test instruction transmitted from a controller; receiving, by the testing apparatus,
(Continued)

movement state information of the pupil that is transmitted from the eye movement tracking system; and determining, by the testing apparatus, the movement trajectory of the pupil according to the movement state information, wherein the controller is a component that is associated with the head-mounted testing equipment and communicatively connected to the testing apparatus of the electronic equipment.

20 Claims, 3 Drawing Sheets (51) Int. Cl.
  *A61B 3/113*   (2006.01)
  *H04B 1/3827*   (2015.01)
  *A61B 90/50*   (2016.01)
(52) U.S. Cl.
  CPC ........ *H04B 1/385* (2013.01); *A61B 2090/502* (2016.02); *H04B 2001/3866* (2013.01)
(58) Field of Classification Search
  USPC .......................................... 351/209
  See application file for complete search history.

(56) References Cited

FOREIGN PATENT DOCUMENTS

| | | |
|---|---|---|
| CN | 101730500 A | 6/2010 |
| CN | 106037626 A | 10/2016 |
| CN | 206120295 U | 4/2017 |
| CN | 107169309 A | 9/2017 |
| WO | 9921474 A1 | 5/1999 |
| WO | 2016072272 A1 | 5/2016 |

OTHER PUBLICATIONS

National Intellectual Property Administration of the P.R.China, Notification of the Second Office Action for Chinese Patent Application No. 2017106149174, dated Jan. 31, 2018, 10 pages (including English translation).

The State Intellectual Property Office of P.R. China, Written Opinion of the Intelectual Searching Authority, dated Aug. 17, 2018, 10 pages (including English translation).

* cited by examiner

VISUAL FIELD TESTING METHOD, SYSTEM, AND TESTING APPARATUS BASED ON HEAD-MOUNTED TESTING EQUIPMENT

This application is a national phase application of International Application No. PCT/CN2018/089606, filed Jun. 1, 2018, which claims priority to China Patent Application No. 201710614917.4, filed on Jul. 26, 2017 at China Patent Office and entitled "Visual Field Testing Method, System, and Testing Apparatus Based on Head-Mounted Testing Equipment," each of which is hereby incorporated by reference in its entirety.

TECHNICAL FIELDS

The present disclosure relates to the technical field of medical testing, and more particularly relates to a visual field testing method and system, and testing apparatus based on head-mounted testing equipment.

BACKGROUND

A visual field refers to an entire spatial region that can be observed when an eye looks at an object. A room for visual field tests is a commonly used means for ophthalmological testing to find visual field defects caused by diseases.

At present, the most commonly used visual field inspection means in clinical medicine is computerized perioptometry. The theoretical basis is a threshold measurement method, that is, the size of a visual field range and a defect are determined according to the different sensitivity of a subject to light in a desired testing range. A specific operation method includes that: first, fixed background brightness is adjusted in testing equipment; second, one eye of a patient is covered, and the uncovered eye is tested; third, the head of the subject is fixed; fourth, the subject is made to actively look at one fixed point; fifth, a testing process is started, and at this time, stimulation points with different brightness will appear in a set testing range; sixth, the subject actively responds to the stimulations through an indicator after sensing the stimulations; seventh, after the single eye test is completed, the eye that has been tested is covered, and the opposite eye is tested by the same testing method above; and eighth, finally, a visual field inspection report of the two eyes is made according to the reactions obtained from the both eyes of the subject.

The above-mentioned testing method involves a complicated testing process and requires fixture of the head of the subject during the test, which may cause discomfort to the subject during the test. In order to guarantee a smooth visual field test, the inspection room needs to be kept in a dark state during the test, which may cause inconvenience to equipment operators.

SUMMARY

In view of the deficiencies in the prior art, the present disclosure provides methods, systems, and testing apparatus for performing visual field tests based on head-mounted testing equipment, which are suitable for testing and can make a subject of a test more comfortable.

According to a first aspect, the present disclosure provides a method for performing a visual field test based on head-mounted testing equipment, including:

transmitting, by testing apparatus in electronic equipment, a start notification for starting monitoring of a movement trajectory of a pupil of a current eye to be tested to an eye movement tracking system after receiving a start test instruction transmitted from a controller;

receiving, by the testing apparatus, movement state information of the pupil that is transmitted from the eye movement tracking system; and determining, by the testing apparatus, the movement trajectory of the pupil according to the movement state information.

The controller is a component that is associated with the head-mounted testing equipment and communicatively connected to the testing apparatus of the electronic equipment.

Optionally, the step of receiving, by the testing apparatus of the pupil, the movement state information, transmitted from the eye movement tracking system may include:

receiving, by the testing apparatus, distance information between the center of the pupil and a center point transmitted from the eye movement tracking system, wherein the center point appears in a visual field of the head-mounted testing equipment and belongs to a pre-displayed reference element for assisting in acquiring the movement trajectory of the pupil of the electronic equipment;

or, receiving, by the testing apparatus, information and indicating that the pupil is switched from a first state to a second state or from a second state to a first state, transmitted from the eye movement tracking system;

or, receiving, by the testing apparatus, a plurality of images transmitted from the eye movement tracking system within a preset time period, wherein each of the images includes position information/distance information of the center of the pupil and the center point.

Optionally, the method further includes:

receiving, by the testing apparatus, first prompt information transmitted from the eye movement tracking system, wherein the first prompt information is information transmitted when the eye movement tracking system determines that a distance between the center of the pupil in at least one image and the center point is greater than a preset threshold within a first preset time period, and is used for prompting adjusting the center of the pupil of the eye to be tested; and transmitting, by the testing apparatus according to the first prompt information, a first alarm signal for prompting the subject to adjust the center of the pupil of the eye to be tested.

Optionally, the method further includes:

receiving, by the testing apparatus, second prompt information transmitted from the eye movement tracking system, wherein the second prompt information is information transmitted for indicating that normal monitoring is executable, when the eye movement tracking system determines that a distance between the center of the pupil of at least one image and the center point is less than or equal to the preset threshold within a second preset time period;

or, receiving, by the testing apparatus, second prompt information transmitted from the eye movement tracking system, wherein the second prompt information is information transmitted for prompting that normal monitoring is executable, when the eye movement tracking system determines that a distance between the center of the pupil of at least one image and the center point is less than or equal to the preset threshold within a second preset time period; and transmitting, by the testing apparatus according to the second prompt information, a second alarm signal for prompting the subject.

Optionally, the method further includes:

transmitting, by the testing apparatus, third prompt information for prompting the subject to adjust the center of the pupil of the eye to be tested to be aligned with the imaging center point after receiving the start test instruction transmitted from the controller, wherein the center point appears in the visual field of the head-mounted testing equipment, and belongs to a pre-displayed reference element for assisting in acquiring the movement trajectory of the pupil of the electronic equipment.

Optionally, before the step of receiving, by the testing apparatus, the start test instruction transmitted from the controller, the method further includes:

acquiring, by the testing apparatus, an identity label of the subject; and correspondingly, receiving the start test instruction after acquiring the identity label.

Specifically, the testing apparatus acquires the identity label of the subject according to iris information of the current eye to be tested of the subject, and then receives the start test instruction after acquiring the identity label.

Optionally, the method further includes:

displaying a preset image video on a screen of the electronic equipment when the testing apparatus determines that the pupil of the eye to be tested is in a normal monitoring state;

or, receiving, by the testing apparatus, at least one image transmitted from the eye movement tracking system, and displaying a preset image video on a screen of the electronic equipment when the testing apparatus determines that the eye to be tested is in a normal monitoring state according to a movement state of the pupil of the at least one image;

or, displaying a preset image video on a screen of the electronic equipment when the testing apparatus determines that the pupil of the eye to be tested is in a normal monitoring state after receiving the second prompt information transmitted from the eye movement tracking system;

and, pausing the display of the image video when the testing apparatus determines that the pupil of the eye to be tested is in an abnormal monitoring state;

or, receiving, by the testing apparatus, at least one image transmitted from the eye movement tracking system, and pausing the display of the image video when the testing apparatus determines that the eye to be tested is in an abnormal monitoring state according to the movement state of the pupil of the at least one image;

or, pausing the display of the image video when the testing apparatus determines that the pupil of the eye to be tested is in an abnormal monitoring state after receiving the first prompt information transmitted from the eye movement tracking system.

Optionally, after the step of receiving, by the testing apparatus, the start test instruction, the method further includes:

receiving stimulation point notification information transmitted from the controller, wherein the stimulation point notification information is obtained by triggering the controller when the pupil of the eye to be tested finds that at least one stimulation point appears in the visual field of the head-mounted testing equipment; and wherein the stimulation point is an element included in each image video frame of the image video.

Optionally, the testing apparatus generates a test report by the determined movement trajectory of the pupil;

and/or, the testing apparatus transmits an end signal after the image video is played completely and transmits stop test information to the eye movement tracking system.

According to a second aspect, the present disclosure provides a system for performing visual field tests based on head-mounted testing equipment, including:

electronic equipment including testing apparatus, the head-mounted testing equipment and an eye movement tracking system.

The electronic equipment is located in the head-mounted testing equipment, and image information in a screen of the electronic equipment is displayed within a visual field range of the head-mounted testing equipment.

The electronic equipment is communicatively connected to a controller associated with the head-mounted testing equipment to receive a signal transmitted when a subject triggers the controller.

The testing apparatus of the electronic equipment executes any of the above methods.

According to a third aspect, the present disclosure provides a system for performing visual field tests based on head-mounted testing equipment, including:

electronic equipment including a testing apparatus and an eye movement tracking system, and the head-mounted testing equipment.

The electronic equipment is located in the head-mounted testing equipment, and image information in a screen of the electronic equipment is displayed within a visual field range of the head-mounted testing equipment.

The electronic equipment is communicatively connected to a controller associated with the head-mounted testing equipment to receive a signal transmitted when a subject triggers the controller.

The testing apparatus of the electronic equipment executes the method according to the first aspect of the present disclosure.

According to a fourth aspect, the present disclosure provides a use method based on the system for performing visual field tests describe above, including:

receiving, by testing apparatus of electronic equipment, a start instruction triggered by a user, then displaying a predicted image of an eye to be tested, and inserting the electronic equipment into head-mounted testing equipment to display image information in a screen of the electronic equipment within a visual field of the head-mounted testing equipment;

when the visual field of the head-mounted testing equipment is arranged in front of the eye of a subject, adjusting a focal length button of the head-mounted testing equipment such that image information seen by a pupil of the eye to be tested of the subject is clearest; and starting a testing process after the controller transmits a start test instruction upon receiving the trigger of the subject.

According to a fifth aspect, the present disclosure provides electronic equipment, including:

a processor suitable for realizing various instructions; and a memory suitable for storing a plurality of instructions suitable for being loaded and executed by the processor.

The electronic equipment is configured to transmit a start notification for starting monitoring of a movement trajectory of a pupil of a current eye to be tested to an eye movement tracking system after receiving a start test instruction transmitted from a controller;

receive movement state information, transmitted from the eye movement tracking system, of the pupil; and determine the movement trajectory of the pupil according to the movement state information.

The controller is a component that is associated with head-mounted testing equipment and communicatively connected to testing apparatus of the electronic equipment.

Compared with the prior art, the technical solutions of the present disclosure have the following advantages:

Compared with a visual field testing method in the prior art, the visual field testing method of the present disclosure is simple in testing manner and convenient to operate, and the subject does not need to fix his head in the testing process, so that the comfort of the subject is improved.

In addition, in the testing process of the present embodiment, the test report of the eye to be tested can be acquired through cooperative use of the electronic equipment and visual reality (VR) glasses, and the present embodiment can be popularized and used.

Further, the background brightness in the testing process of the present embodiment, the color of a center fixation point, and the like can be adjusted and configured according to a condition of the subject, and it is not limited to a dark environment, so that the test is convenient, quick and comfortable.

Specifically, compared with a conventional visual field analyzer, a head-mounted VR visual field analyzer in the visual field testing system in the present disclosure further has the following advantages: 1, large-sized active equipment is minimized (which can be used in a power-free area); 2, the head-mounted VR visual field analyzer is movable, so as to be popularized in the public; 3, the eye movement tracking can avoid a wrong result caused by subjective reasons of the subject; and 4, the traceability of test data realizes healthy management of eyes.

DETAILED DESCRIPTION OF THE EMBODIMENTS

In order to make the objectives, technical solutions and advantages of the embodiments of the present disclosure clearer, the technical solutions in the embodiments of the present disclosure will be described clearly and completely below in connection with the drawings in the embodiments of the present disclosure. Obviously, the embodiments described herein are part of the embodiments of the present disclosure, not all the embodiments. Based on the embodiments in the present disclosure, all other embodiments obtained by those of ordinary skilled in the art without creative efforts shall fall within the protection scope of the present disclosure.

Embodiment I

Figure 1:
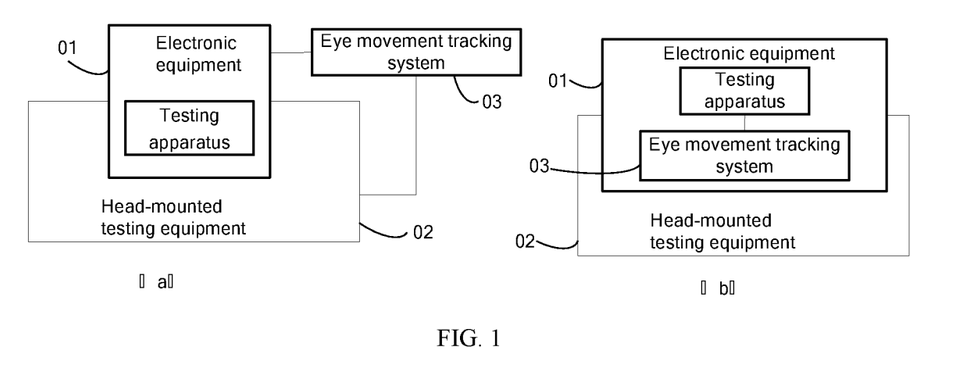
FIG. 1 is a schematic structural diagram of a system for performing visual field tests based on head-mounted testing equipment in accordance with an embodiment of the present disclosure.

As shown in FIG. 1, the embodiment of the present disclosure provides a system for performing visual field tests based on head-mounted testing equipment. The system for performing visual field tests in accordance with the present embodiment may include: electronic equipment 01, head-mounted testing equipment 02, and an eye movement tracking system 03.

The eye movement tracking system 03 may be located in any electronic equipment independent from the electronic equipment 01 described above (as shown in FIG. 1(*a*)) or may be located in the electronic equipment 01 (as shown in FIG. 1(*b*)). The present embodiment does not limit the position and may be adjusted according to actual needs.

It should be noted that when the eye movement tracking system 03 may be independent from the electronic equipment 01, the eye movement tracking system 03 may communicate with a testing apparatus in the electronic equipment 01 and may be located in the head-mounted testing equipment 02 to acquire a movement state of a pupil of an eye to be tested of a subject in real time, for example, by acquiring a plurality of images of the pupil of the eye to be tested of the subject through an infrared imaging photographing method. Or the eye movement tracking system 03 may be connected with an imaging apparatus of the head-mounted testing equipment 02 to control the imaging apparatus to acquire the movement state of the pupil of the eye to be tested of the subject in real time. The present embodiment may be adjusted according to actual needs.

The electronic equipment 01 of the present embodiment may be integrated with the testing apparatus, i.e., an application program for testing the eye to be tested of the subject. In addition, the eye movement tracking system 03 may also be integrated with the electronic equipment 01 and may be also an application program for acquiring a movement trajectory of the pupil of the eye to be tested. At this time, the testing apparatus in the electronic equipment 01 may interact with the eye movement tracking system 03 to perform a test on the eye to be tested of the subject.

In use, the electronic equipment 01 described above may be located in the head-mounted testing equipment 02, and image information may be displayed on a screen of the electronic equipment within a visual field range of the head-mounted testing equipment.

The electronic equipment 01 in accordance with the present embodiment may be a mobile phone, an IPAD or other equipment with display screens. The head-mounted testing equipment 02 may be virtual reality (VR) glasses, a VR visual field analyzer, or a VR tester, and the present embodiment is not limited thereto.

In some embodiments of the present disclosure, the visual field testing range of the subject may depend on the size of the visual field of the head-mounted testing equipment, such as the VR glasses. For example, the visual field testing range may reach about 40 degrees in an up direction, a down direction, a left direction, and a right direction, and may be finally up to actual equipment.

For example, when the electronic equipment is a mobile phone, the mobile phone may be inserted into the head-mounted testing equipment 02. The head-mounted testing equipment 02 in the present embodiment may be the VR glasses/the VR visual field analyzer.

In addition, the current head-mounted testing equipment may be associated with a controller, such as a common hand shank. When the electronic equipment 01 is located in the head-mounted testing equipment 02 for testing, the electronic equipment is communicatively connected to the controller associated with the head-mounted testing equipment, so as to receive a signal transmitted when the subject triggers the controller.

Generally, the hand shank may be connected to the testing apparatus in the electronic equipment 01 through Bluetooth as to facilitate communication.

In a specific testing process, a method of using the system for performing visual field tests as described above may include the following steps.

First step: an input interface of the testing apparatus may receive relevant parameters input by a user after the testing apparatus of the electronic equipment 01 receives a start instruction triggered by the user, and a predicted image of the eye to be tested is displayed on a testing interface after the parameter setting is completed.

The start instruction of this step may be understood as an instruction that the user triggers the testing apparatus to be turned on through a screen of the mobile phone. For example, the user double clicks an icon corresponding to the testing apparatus in a touch display screen of the electronic equipment, and the testing apparatus is then turned on.

After the testing apparatus is turned on, the mobile phone may be used to take a picture to acquire a head portrait of the subject/an image of the eye to be tested. The subject may manually type in user information (name, sex, age, file label, remarks, identity card information and the like) or set other testing related parameters in the input interface of the testing apparatus and enter the testing interface.

Other testing related parameters may include: the number of the tested eye, the color (red, yellow), etc. of a stimulation light source, duration of stimulation points, the interval time of the stimulation points and the like.

In addition, in the present embodiment, the above-mentioned predicted image of the eye to be tested may be an image of a center point/center dot displayed in a white background. The image information may partially reflect the other testing related parameters. The center point/center dot may be a pre-displayed reference element for assisting in acquiring the movement trajectory of the pupil of the electronic equipment.

Second step, the electronic equipment is inserted into the head-mounted testing equipment, so that the image information, i.e., the image information of the testing interface, in the screen of the electronic equipment is displayed in the visual field of the head-mounted testing equipment.

For example, after the mobile phone is inserted into the VR glasses, the position of the mobile phone may be adjusted, and a patient may wear the VR glasses with the inserted mobile phone.

Third step, when the head-mounted testing equipment is arranged in front of the eye of the subject, a focal length button of the head-mounted testing equipment may be adjusted such that the image information seen by the pupil of the eye to be tested of the subject is clearest.

Fourth step, a testing process is started after the controller transmits the start test instruction upon receiving the trigger of the subject. That is, the position of the pupil of the eye to be tested of the subject is tracked and calibrated, and a photo of an eye is taken.

That is, the subject may adjust the focal length of the VR glasses through an adjustment knob (such as a focal length adjustment knob) on the VR glasses, so as to adjust the center dot in the image information to the highest definition, and then the subject operates the controller, i.e., the hand shank, to proceed to the next step. At this time, the testing apparatus may inform the eye movement tracking system in the background to start to monitor the state of the eye.

The eye movement tracking system may be operated in the background, and may select an infrared imaging manner to acquire images, in order to monitor a movement trajectory of a pupil of a single eye of the subject wearing the VR glasses and a blinking state in real time.

It should be noted that the system for performing visual field tests in accordance with the present embodiment may selectively test a single eye only or test two eyes simultaneously. When two eyes are tested, one of the eyes is tested at first, and then the testing apparatus can automatically start to test the other eye. A doctor and the patient/subject do not need to carry out any operations, and the test operations are all automatically completed.

Specifically, the testing apparatus acquires an identity label of the subject before being inserted into the head-mounted testing equipment, such as the VR glasses, and receives the start test instruction after acquiring the identity label.

For example, the testing apparatus may acquire a picture of the current eye to be tested of the subject, and regard an iris of the eye to be tested in the picture as a unique label of the eye to be tested, so as to be used in generation of a test report.

Or, for example, the testing apparatus receives an identity label input by the subject. Generally, in a visual field testing technology, the iris may be used as an identification label.

It can be understood that a human eye structure is composed of a sclera, an iris, a pupillary crystalline lens, retina and other portions. The iris is a circular-ring portion located between the black pupil and the white sclera, and contains many staggered spots, filaments, corona, stripes, recesses and other detailed features. These features may define the uniqueness of the iris feature and may also define the uniqueness of the identity identification. Therefore, the features of the iris of the eye may be used for the identity identification of the eye to be tested of each subject.

A testing process of the VR glasses with the mobile phone is described below in combination with FIGS. 2 and 3.

Figure 2:
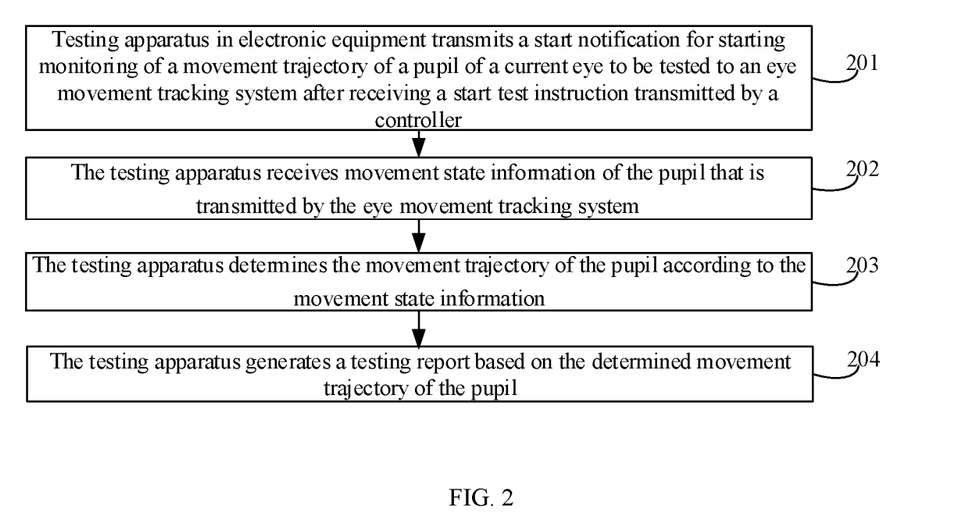
FIG. 2 and FIG. 3 are respectively schematic flow diagrams of a method for performing visual field tests based on head-mounted testing equipment in accordance with an embodiment of the present disclosure.

Specifically, referring to FIG. 2, a method for performing visual field tests based on head-mounted testing equipment of the present embodiment may include the following steps.

201. Testing apparatus located in electronic equipment transmits, to an eye movement tracking system, a start notification for starting monitoring of a movement trajectory of a pupil of a current eye to be tested after receiving a start test instruction transmitted from a controller. For example, the eye movement tracking system may receive a communication signal for starting to test a left eye or right eye that is transmitted from the testing apparatus.

It should be understood that the controller in accordance with the present embodiment may be a component that is associated with the head-mounted testing equipment and communicatively connected to the testing apparatus of the electronic equipment.

It should be noted that the testing apparatus may acquire an identity label of a subject after receiving the start test instruction. For example, the testing apparatus pre-acquires iris information of the current eye to be tested of the subject as the identity label of the subject, and then receives the start test instruction after acquiring the identity label. That is, a picture of the current eye to be tested of the subject may be taken in advance, and the iris information may be identified from the picture.

In addition, before the testing apparatus receives the start test instruction, the testing apparatus may acquire the identity label of the subject and transmit an instruction for acquiring the iris information to the eye movement tracking system. The eye movement tracking system may take a picture of the eye to be tested according to the instruction and may transmit the picture to the testing apparatus. As such, the testing apparatus may identify the iris information according to the picture to generate the identity label of the eye to be tested to guarantee the uniqueness of the eye to be tested, and may effectively store a test report according to the identity label.

202. The testing apparatus may receive movement state information of the pupil that is transmitted from the eye movement tracking system.

For example, the testing apparatus may receive distance information of a distance between the center of the pupil and a center point transmitted from the eye movement tracking system. The center point may appear in a visual field of the head-mounted testing equipment and may belong to a pre-displayed reference element for assisting in acquiring the movement trajectory of the pupil of the electronic equipment.

Or, the testing apparatus may receive information indicating that the pupil is switched from a first state to a second state or from the second state to the first state, which is transmitted from the eye movement tracking system. The first state here may be understood as an open state of the eye to be tested, and the second state may be understood as a closed state of the eye to be tested.

Or, the testing apparatus receives a plurality of images transmitted from the eye movement tracking system within a preset time period. Each of the images may include position information/distance information of the center of the pupil and the center point. The testing apparatus may then determine the movement state information of the pupil according to the distance information in all the images.

In practice, if the testing apparatus receives the information indicating that the pupil is switched from the first state to the second state or from the second state to the first state, transmitted from the eye movement tracking system, the testing apparatus may transmit prompt information for prompting a state change of the subject.

203. The testing apparatus may determine the movement trajectory of the pupil according to the movement state information.

Optionally, the method may further include step 204 described below.

204. The testing apparatus may generate the test report based on the determined movement trajectory of the pupil.

The test report in accordance with the present embodiment may include: a start point of the test, an end point of the test, a pause time point during the test, the number of the tested eye, the movement trajectory of the pupil of the tested eye, other information of the pupil of the tested eye, and the like. The present embodiment does not limit the content of the test report and may make adjustments according to actual needs.

It should be noted that the testing apparatus may determine the iris in the eye to be tested as being a unique identity identification label. That is, the test report may include the iris information. For example, the testing apparatus may identify the iris information included in the picture transmitted from the eye movement tracking system, and may then determine the iris information as being the label of the eye to be tested.

Compared with a testing method in the prior art, the method in accordance with the present embodiment can provide a simple testing process and can improve the comfort of the subject during the test, improve the testing accuracy of the subject and enhance user experience.

Figure 3:
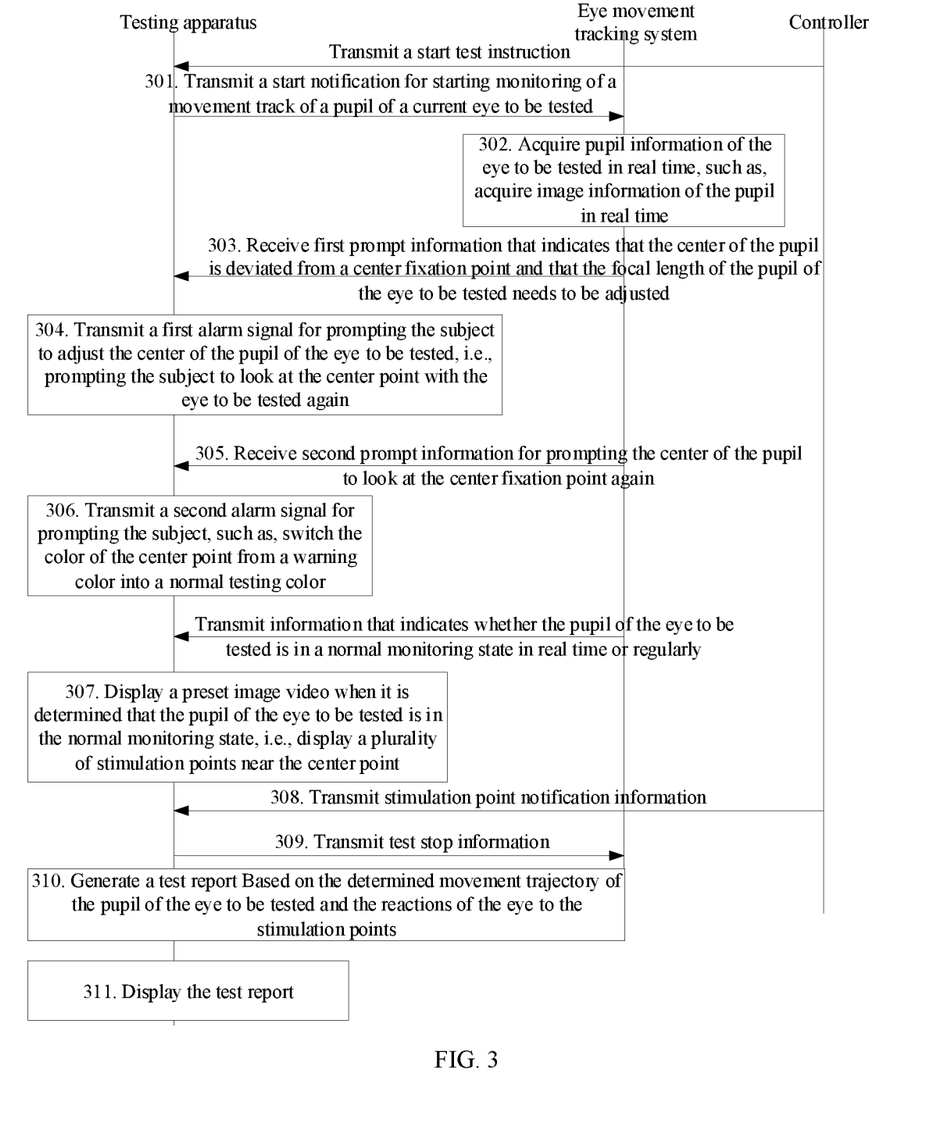

Referring to FIG. 3, a method for performing visual field tests based on head-mounted testing equipment of the present embodiment may include the following.

301. Testing apparatus transmits a start notification for starting monitoring of a movement trajectory of a pupil of a current eye to be tested to an eye movement tracking system after receiving a start test instruction transmitted from a controller.

For example, if the testing apparatus receives the start test instruction transmitted from the controller, but the pupil of the eye to be tested of a subject is not aligned with the center dot described above, and at this time, the testing apparatus may transmit third prompt information for prompting the subject to adjust the center of the pupil of the eye to be tested to be aligned with the imaging center point, such as voice prompt information.

After the eye movement tracking system receives an instruction for starting to test a left eye or right eye, such as a test start communication signal, the testing apparatus may further prompt a wearer to adjust the sight to be aligned with the center point of imaged content using voices or VR imaging content. After the eye movement tracking system detects the alignment, the visual field test is started by counting down a preset time period, such as 3 seconds.

The VR imaging characters described herein may be displayed on a screen of the electronic equipment and may be visible within the VR visual field.

It should be noted that the center point may appear in the visual field of the head-mounted testing equipment and may belong to a pre-displayed reference element for assisting in acquiring the movement trajectory of the pupil of the electronic equipment.

302. The eye movement tracking system may acquire pupil information of the eye to be tested of the subject in real time after receiving the start notification.

The eye movement tracking system in accordance with the present embodiment may acquire pupil image information in real time using an infrared imaging method and may analyze the image information to acquire movement state information of the pupil, such as, monitoring a movement trajectory of the pupil of a single eye of the wearer and a blinking state in real time.

303. The testing apparatus may receive first prompt information transmitted from the eye movement tracking system when the center of the pupil of the eye of the subject that is to be tested is deviated from the center dot, wherein the first prompt information is information transmitted when the eye movement tracking system determines that a distance between the center of the pupil of at least one image and the center point is greater than a preset threshold within a first preset time period, and may be used for prompting adjustment of the center of the pupil of the eye to be tested.

For example, when the eye movement tracking system is in an operating state, the center point of the imaged content in the VR virtual test is used as a main corresponding monitoring region. When the movement trajectory of the pupil of the wearer leaves the center point (+/−0.5 mm), the first prompt information is transmitted. When the movement trajectory of the pupil of the wearer returns to the center point, second prompt information as described below is transmitted.

304. The testing apparatus may further transmit, according to the first prompt information, a first alarm signal for prompting the subject to adjust the center of the pupil of the eye to be tested.

For example, the testing apparatus may switch the color of the center fixation point of the eye to be tested into a warning color, such as red. As such, the first alarm signal is transmitted.

For example, the eye movement tracking system may determine a position state of an eyeball of the pupil, i.e., the center of the pupil, in real time after starting the monitoring. When the eyeball is not located near the center point, the testing apparatus may display the center dot on the screen of the electronic equipment in red. And at this time, the wearing position of the VR glasses needs to be adjusted, or the subject needs to adjust the state of the pupil of the eye to be tested till the center dot turns into green. That is, the eyeball is located near the center point, i.e., a first region.

305. The testing apparatus may receive the second prompt information transmitted from the eye movement tracking system when the center of the pupil of the eye of the subject that is to be tested returns to the center dot from the deviated state, wherein the second prompt information is information transmitted to indicate that normal monitoring is executable, when the eye movement tracking system determines that a distance between the center of the pupil of at least one image and that the center point is less than or equal to the preset threshold within a second preset time period.

306. The testing apparatus may transmit, according to the second prompt information, a second alarm signal to notify the subject.

For example, the testing apparatus switches the color of the center fixation point of the eye to be tested from the warning color into a normal testing color.

307. A preset image video is displayed on the screen of the electronic equipment when the testing apparatus determines that the pupil of the eye to be tested is in a normal monitoring state.

The image video in accordance with the present embodiment may include at least one stimulation point that appears in a second region near to the center point. For example, the image information included in the image video may include stimulation points that appear randomly around the center point in a flickering manner.

For example, the testing apparatus may determine that the pupil of the eye to be tested is in the normal monitoring state after receiving the second prompt information. Or the testing apparatus receives at least one image transmitted from the eye movement tracking system, and determines whether the eye to be tested is in the normal monitoring state according to a movement state (i.e., the distance between the center of the pupil and the center point) of the pupil of the at least one image.

308. The testing apparatus receives stimulation point notification information transmitted from the controller, wherein the stimulation point notification information is obtained by triggering the controller when the pupil of the eye to be tested finds that at least one stimulation point appears in the visual field of the head-mounted testing equipment, and the stimulation point is an element included in each image video frame in the image video.

It can be understood that in the visual field testing process, there is a dot that is always bright in the center of the visual field of the VR glasses, i.e., the center dot. To test a fixed view point, the subject keeps the eye to be tested looking at this dot. The stimulation points appear randomly around this dot in a flickering manner. When the subject keeps the eye to be tested looking at the center fixed view point, the subject presses the controller in the hand immediately in case of seeing the emerging stimulation points.

In specific applications, after the stimulation point appears at each time, if the subject presses the controller only once within a certain time period, the testing apparatus may determine that the patient can perceive this stimulation point. If the subject does not press the controller within the certain time period, the testing apparatus may determine that the subject cannot perceive this stimulation point. If the subject presses the controller for multiple times, the testing apparatus may determine that the subject presses the controller by mistake, and the stimulation point is re-tested in a subsequent test.

309. The testing apparatus transmits an end signal after the image video is played completely and transmits stop test information to the eye movement tracking system.

After all the stimulation points are tested, the test is ended. The testing apparatus may prompt the subject to take off the equipment. In case of any special situations in the test, the equipment may be taken off in the middle of the test, and then the test is ended manually. At the end of the test, the testing apparatus may inform the eye movement tracking system to stop testing the state of the eye.

310. The testing apparatus may generate a test report based on the determined movement trajectory of the pupil, reactions of the eye to be tested to the stimulation points, and the like.

The test report in the present embodiment may include: a testing result of each tested point (displayed in a manner of a polar coordinate system: visible points are green, and invisible points are red); the total number of the tested points (not include repeatedly tested points), the number of the visible points and the number of the invisible points; a testing duration; the number of times of pausing the test in the testing process; the number of the repeatedly tested points in the testing process; the total number of times of pressing the controller by the subject in the testing process, and the like.

It can be understood that the testing apparatus may regard the iris in the eye to be tested as being a unique identity identification label. That is, the test report may include the iris information. For example, the testing apparatus may identify the iris information included in the picture transmitted from the eye movement tracking system, and may then regard the iris information as being the label of the eye to be tested.

Or the testing apparatus may pre-acquire a picture of the eye to be tested of the subject before starting the test of the subject and may acquire the iris information from the picture for unique identity identification. The test report generated at each time may include an identity identification label of the iris.

311. The testing apparatus may show a user, such as a doctor or the subject, the test report.

That is, the testing result may be selected to be saved and uploaded, or is not be saved, and another test may be carried out.

After the above step 308, the display of the image video may be paused when the testing apparatus determines that the pupil of the eye to be tested is in an abnormal monitoring state.

Or the testing apparatus may receive at least one image transmitted from the eye movement tracking system and may pause the display of the image video when the testing apparatus determines that the eye to be tested is in an abnormal monitoring state according to the movement state of the pupil in the at least one image.

Or the display of the image video may be paused when the testing apparatus determines that the pupil of the eye to be tested is in an abnormal monitoring state after receiving the first prompt information transmitted from the eye movement tracking system.

In one optional implementation, before the image video is played as described above, i.e., before the stimulation point appears at each time, the testing apparatus may determine whether the pupil of the eye to be tested is in the normal monitoring state according to the movement state of the pupil of the eye movement tracking system. If the pupil is in the normal monitoring state, i.e., at least three states of the eye are all normal, the image video may be played. At this time, the stimulation point appears in the VR visual field, and the center point may be kept in green.

If the testing apparatus determines that the pupil is in the abnormal monitoring state according to the movement state of the pupil of the eye movement tracking system, the playback of the image video may be paused, i.e., the stimulation point is paused to appear. And at this time, the first alarm signal may be sent, namely the center point turns into red. The above process of determining whether the state of the pupil of the eye to be tested is in the normal monitoring state according to the movement state of the pupil of the eye movement tracking system may be repeated until the subject adjusts the state of the pupil of the eye to be tested.

In addition, after step 302, in the operating state of the eye movement tracking system, the closed and open states of the eye of the wearer may be monitored in real time. When the eye to be tested of the subject is detected as being closed, closed-eye prompt information or the second state prompt information may be transmitted to the testing apparatus. When the eye of the subject is detected as being open after closed, open-eye-after-closed-eye prompt information or the first state prompt information may be transmitted to the testing apparatus.

The visual field testing method in accordance with the present embodiment is simple in testing manner and convenient to operate, and the subject does not need to fix his head in the testing process, so that the comfort of the subject is improved.

Further, the background brightness in the testing process in accordance with the present embodiment, the color of a center fixation point, and the like can be adjusted and configured according to a condition of the subject, and it is not limited to a dark environment, so that the test is convenient, quick and comfortable.

Figure 4:
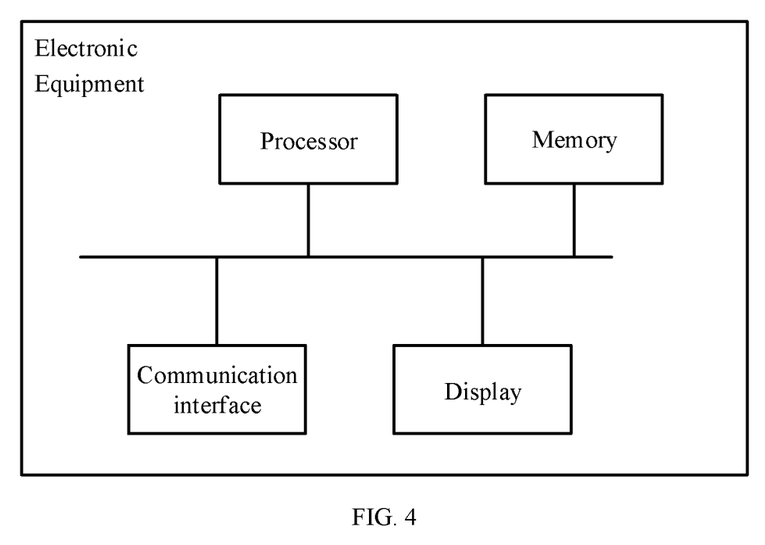
FIG. 4 is a schematic structural diagram of electronic equipment in accordance with an embodiment of the present disclosure.

In addition, referring to FIG. 4, the embodiments of the present disclosure further provide electronic equipment, including:

a processor, suitable for realizing various instructions; and a memory, suitable for storing a plurality of instructions suitable for being loaded and executed by the processor.

The electronic equipment is configured to transmit a start notification for starting monitoring of a movement trajectory of a pupil of a current eye to be tested to an eye movement tracking system after receiving a start test instruction transmitted from a controller;

receive movement state information, transmitted from the eye movement tracking system, of the pupil; and determine the movement trajectory of the pupil according to the movement state information; and the controller is a component that is associated with head-mounted testing equipment and communicatively connected to testing apparatus of the electronic equipment.

It can be understood that the processor of the present embodiment may execute the method shown in FIGS. 2-3 referring to the description above. The description of the present embodiment does not repeat the description above.

The electronic equipment of the present embodiment is matched with a head-mounted tester to acquire the test report of the eye to be tested, so that the test is convenient, and the cost is reduced. Therefore, the electronic equipment may be better popularized and used.

The electronic equipment of the present embodiment may execute the method shown in FIGS. 2-3, and details refer to the above content, so that descriptions thereof are omitted.

Figure 5:
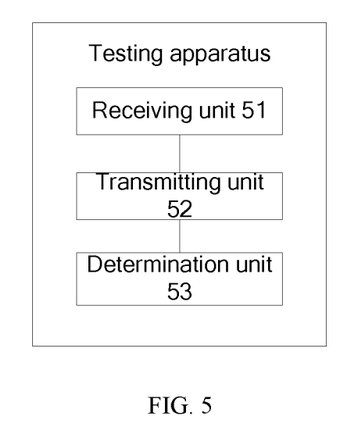
FIG. 5 is a schematic structural diagram of testing apparatus in accordance with an embodiment of the present disclosure.

In addition, referring to FIG. 5, the embodiments of the present disclosure further provide testing apparatus, including:

a receiving unit 51, configured to receive a start test instruction transmitted from a controller, wherein the controller is a component that is associated with head-mounted testing equipment and communicatively connected to the testing apparatus of electronic equipment; a transmitting unit 52, configured to transmit a start notification for starting monitoring of a movement trajectory of a pupil of a current eye to be tested to an eye movement tracking system, wherein the receiving unit 51 is further configured to receive movement state information, transmitted from the eye movement tracking system, of the pupil; and a determination unit 53, configured to determine the movement trajectory of the pupil according to the movement state information.

For example, the receiving unit 51 may be configured to receive distance information between the center of the pupil and a center point transmitted from the eye movement tracking system, wherein the center point appears in a visual field of the head-mounted testing equipment, and belongs to a pre-displayed reference element for assisting in acquiring the movement trajectory of the pupil of the electronic equipment.

Or the receiving unit 51 may be configured to receive information indicating that the pupil is switched from a first state to a second state or from a second state to a first state, transmitted from the eye movement tracking system;

Or the receiving unit 51 may be configured to receive a plurality of images transmitted from the eye movement tracking system within a preset time period, wherein each image includes position information/distance information of the center of the pupil and the center point.

In a specific implementation process, the receiving unit 51 may further be configured to receive first prompt information transmitted from the eye movement tracking system, wherein the first prompt information is information transmitted when the eye movement tracking system determines that a distance between the center of the pupil of at least one image and the center point is greater than a preset threshold within a first preset time period, and used for prompting adjustments of the center of the pupil of the eye to be tested.

The transmitting unit 52 may further be configured to transmit, according to the first prompt information, a first alarm signal for prompting a subject to adjust the center of the pupil of the eye to be tested. For example, the color of a center fixation point of the eye to be tested is switched into a warning color.

In another optional implementation, the receiving unit 51 may further be configured to receive second prompt information transmitted from the eye movement tracking system, wherein the second prompt information is information transmitted for prompting that normal monitoring is executable, when the eye movement tracking system determines that a distance between the center of the pupil of at least one image and the center point is less than or equal to the preset threshold within a second preset time period.

Or the receiving unit 51 may further be configured to receive second prompt information transmitted from the eye movement tracking system, wherein the second prompt information is information transmitted for prompting that normal monitoring is executable, when the eye movement tracking system determines that a distance between the center of the pupil of at least one image and the center point is less than or equal to the preset threshold within a second preset time period.

Correspondingly, the transmitting unit 52 may further be configured to transmit, according to the second prompt information, a second alarm signal for prompting the subject. For example, the color of the center fixation point of the eye to be tested is switched from the warning color into a normal testing color.

In a further optional implementation scene, the transmitting unit 52 may be configured to transmit third prompt information for prompting the subject to adjust the center of the pupil of the eye to be tested to be aligned with an imaging center point after the receiving unit 51 receives the start test instruction transmitted from the controller.

The center point may appear in the visual field of the head-mounted testing equipment and may belong to a pre-displayed reference element for assisting in acquiring the movement trajectory of the pupil of the electronic equipment.

Further, the testing apparatus may further include a video playing unit 54 (not shown in the figure). The video playing unit 54 may display a preset image video on a screen of the electronic equipment when the determination unit 53 determines that the pupil of the eye to be tested is in a normal monitoring state, and the video playing unit 54 may pause the playback of the image video when the determination unit 53 determines that the pupil of the eye to be tested is in an abnormal monitoring state.

The receiving unit 51 may further be configured to receive stimulation point notification information transmitted from the controller, wherein the stimulation point notification information is obtained by triggering the controller when the pupil of the eye to be tested finds that at least one stimulation point appears in the visual field of the head-mounted testing equipment, and the stimulation point is an element included in each image video frame in the image video.

In addition, the transmitting unit 52 may be configured to transmit an end signal after the video playing unit 54 completes playback of the image video and transmit stop test information to the eye movement tracking system.

Optionally, the testing apparatus may further include a test report generation unit that is not shown in the figure. The test report generation unit may be configured to generate a test report by the determined movement trajectory of the pupil.

The testing apparatus of the present embodiment may execute the content of any above-mentioned method embodiments, so descriptions thereof are omitted here. Details refer to the above content.

The testing apparatus of the present embodiment is located in the electronic equipment that is matched with VR glasses to well realize a test on eyes. The complicated testing process in the prior art is simplified, and the cost is reduced. The testing apparatus may be popularized and used.

In accordance with the embodiments provided by the present disclosure, it should be understood that the disclosed related apparatus and methods may be implemented in other manners. For example, the apparatus embodiments described above are merely illustrative. For example, the division of the modules or units may be a logical function division. In actual implementation, there may be another division manner. For example, a plurality of units or components may be combined or integrated into another system, or some features may be ignored or not executed. From another point of view, the mutual coupling or direct coupling or communication connection shown or discussed may be indirect coupling or communication connection through some interfaces, apparatus or units, and may be in electrical, mechanical or other forms. Partial or all units can be selected to achieve the objective of the solution of the present embodiment according to actual needs.

In addition, all functional units in all the embodiments of the present disclosure can be integrated into one processing unit, or each unit can physically exist alone, or two or more units can be integrated in one unit. The above integrated units can be implemented in the form of hardware or can be implemented in the form of software functional units.

The integrated unit, if implemented in the form of a software functional unit and sold or used as a standalone product, may be stored in a computer readable storage medium. Based on this understanding, the technical solutions of the present disclosure essentially or the part that contributes to the prior art or all or part of the technical solution can be embodied in the form of a software product, and the computer software product is stored in a storage medium including a plurality of instructions for causing a processor of electronic equipment to perform all or part of the steps of the method described in various embodiments of the present disclosure. The foregoing storage media include: a U disk, a mobile hard disk, a Read-Only Memory (ROM), a Random-Access Memory (RAM), a magnetic disk or an optical disk and other various media that can store program codes.

Embodiment II

In the system for performing visual field tests based on the head-mounted testing equipment, the electronic equipment is positioned in the head-mounted testing equipment.

In the present embodiment, the electronic equipment described above may also be arranged in the head-mounted testing equipment, such as VR glasses with a built-in screen. This electronic equipment may have a processor, a memory, a power supply or power interface, a communication port and the like. Equivalently, the existing mobile phone or IPAD and the VR glasses are made into an integrated structure. This is also a product of the VR glasses and may also be used to implement the method for performing visual field tests based on the head-mounted testing equipment of the present disclosure. By adoption of this structure, the operations of installing and removing the electronic equipment may be eliminated, so as to avoid damage to the electronic equipment or VR glasses caused by frequent removal and prolong the service life of the electronic equipment or VR glasses.

Embodiment III

On the basis of Embodiment I or Embodiment II, preferably, the electronic equipment may be connected with an interaction component. The interaction component has a display screen to facilitate the operation. The interaction component is in wired or wireless connection with the electronic equipment, and is configured to input set parameters and personal information of the subject before the test, and temporarily adjust the parameters in the testing process, for example, to set whether the first tested eye is the left eye or the right eye, input information indicating whether the subject suffers from achromatopsia, and input an instruction for manually pausing the test. When the subject suffers from the achromatopsia, the colors of the center point and the stimulation point shall be correspondingly changed to avoid the influence on test results. Through the arrangement of this interaction component, it is convenient to input information into and transmit a control instruction to the electronic equipment, and the state of the electronic equipment may be learnt in real time through the display screen to realize interaction. In this way, it is not necessary to take off the electronic equipment or the head-mounted testing equipment and frequently adjust the state of wearing of the VR glasses by the subject. The influence on the testing process is small, and the testing time is shortened.

Embodiment IV

On the basis of the foregoing embodiments, the system for performing visual field tests based on the head-mounted testing equipment may further include a cloud server. The electronic equipment establishes communication connection with the cloud server. The cloud server may be a server of an appointed website. Testing data of a tested visual field range, the personal information of the subject and the like may be all uploaded to the cloud server to realize real-time uploading of the data. When the testing information of all the sets of electronic equipment is uploaded to the same cloud server, the testing results of the subject may not be restricted by districts and hospitals, and personal testing data may be gathered. The subject may also acquire the own testing results or statistical data, analytical data and the like of multiple tests at any time from the cloud server in a way of, for example, logging in an account. A testing mechanism may also provide advice for improving the later visual field range testing method through big data operation of all the testing data.

It should be finally noted that: the above embodiments are only used to describe the technical solutions of the present disclosure, and not intended to limit the present disclosure. Although the present disclosure has been described in detail with reference to the foregoing embodiments, those ordinarily skilled in the art should understand that they can still modify the technical solutions recorded in all the foregoing embodiments, or equivalently replace some of the technical features, and these modifications or replacements do not depart the essences of the corresponding technical solutions from the spirit and scope of the technical solutions of all the embodiments of the present disclosure.

INDUSTRIAL PRACTICABILITY

The present disclosure provides a visual field testing method and system based on head-mounted testing equipment, and testing apparatus. The method includes: the testing apparatus located in electronic equipment transmits a start notification for starting monitoring of a movement trajectory of a pupil of a current eye to be tested to an eye movement tracking system after receiving a start test instruction transmitted from a controller; the testing apparatus receives movement state information, transmitted from the eye movement tracking system, of the pupil; and the testing apparatus determines the movement trajectory of the pupil according to the movement state information. The controller is a component that is associated with the head-mounted testing equipment and communicatively connected to the testing apparatus of the electronic equipment. The above method and system and the testing apparatus can reduce the testing complexity and improve the testing accuracy and comfort and has extremely high industrial practicability.

The invention claimed is:

1. A method for performing a visual field test based on head-mounted testing equipment, comprising:
    transmitting, by a testing apparatus in electronic equipment that is independent from the head-mounted testing equipment, a start notification for starting monitoring of a movement trajectory of a pupil of an eye to be tested to an eye movement tracking system after receiving a start test instruction transmitted from a controller associated with the head-mounted testing equipment and communicatively connected to the testing apparatus in the electronic equipment;
    displaying, by the electronic equipment positioned in the head-mounted testing equipment during the visual field test, image information on a screen of the electronic equipment within a visual field of the head-mounted testing equipment;
    receiving, by the testing apparatus, movement state information of the pupil transmitted from the eye movement tracking system; and
    determining, by the testing apparatus, the movement trajectory of the pupil according to the movement state information.

2. The method according to claim 1, wherein receiving, by the testing apparatus, the movement state information of the pupil transmitted from the eye movement tracking system comprises:
    receiving, by the testing apparatus, at least one of distance information about a distance between a center of the pupil and a center point transmitted from the eye movement tracking system, information indicating that the pupil is switched from a first state to a second state, or a plurality of images transmitted from the eye movement tracking system within a preset time period, wherein the center point appears in a visual field of the head-mounted testing equipment and belongs to a pre-displayed reference element for assisting in acquiring the movement trajectory of the pupil of the electronic equipment, wherein the information indicating that the pupil is switched from the first state to the second state is transmitted from the eye movement tracking system, and
    wherein each of the images comprises position information/distance information of a center of the pupil and a center point.

3. The method according to claim 1, further comprising:
    receiving, by the testing apparatus, first prompt information transmitted from the eye movement tracking system, wherein the first prompt information is information transmitted for prompting adjusting a center of the pupil of the eye to be tested, when the eye movement tracking system determines that a distance between the center of the pupil in at least one image and a center point is greater than a preset threshold within a first preset time period; and
    transmitting, by the testing apparatus according to the first prompt information, a first alarm signal for prompting a subject to adjust the center of the pupil of the eye to be tested.

4. The method according to claim 1, further comprising:
receiving, by the testing apparatus, second prompt information transmitted from the eye movement tracking system, wherein the second prompt information is information transmitted for indicating that normal monitoring is executable, when the eye movement tracking system determines that a distance between a center of a pupil in at least one image and a center point is less than or equal to a preset threshold within a second preset time period.

5. The method according to claim 4, further comprising:
displaying a preset image video on a screen of the electronic equipment when the testing apparatus determines that the pupil of the eye to be tested is in a normal monitoring state.

6. The method according to claim 5, further comprising:
receiving stimulation point notification information transmitted from the controller, wherein the stimulation point notification information is obtained by triggering the controller when a pupil of an eye to be tested finds that at least one stimulation point appears in a visual field of the head-mounted testing equipment, wherein the stimulation point is an element included in each image video frame in the image video.

7. The method according to claim 5, further comprising:
generating, by the testing apparatus, a test report based on the determined movement trajectory of the pupil.

8. The method of claim 5, further comprising:
pausing the display of the image video when the testing apparatus determines that the pupil of an eye to be tested is in an abnormal monitoring state after receiving first prompt information transmitted from the eye movement tracking system.

9. The method of claim 5, further comprising:
transmitting, by the testing apparatus, an end signal after the image video is played and stop test information to the eye movement tracking system.

10. The method of claim 4, further comprising transmitting, by the testing apparatus according to the second prompt information, a second alarm signal for prompting a subject.

11. The method of claim 4, further comprising receiving, by the testing apparatus, at least one image transmitted from the eye movement tracking system, and displaying a preset image video on a screen of the electronic equipment when the testing apparatus determines that an eye to be tested is in a normal monitoring state according to a movement state of the pupil in the at least one image.

12. The method of claim 4, further comprising:
displaying a preset image video on a screen of the electronic equipment when the testing apparatus determines that the pupil of the eye to be tested is in a normal monitoring state after receiving second prompt information transmitted from the eye movement tracking system; and
pausing the displaying of the preset image video when the testing apparatus determines that the pupil of the eye to be tested is in an abnormal monitoring state.

13. The method of claim 4, further comprising:
receiving, by the testing apparatus, at least one image transmitted from the eye movement tracking system, and pausing the display of the image video when the testing apparatus determines that an eye to be tested is in an abnormal monitoring state according to a movement state of a pupil of the at least one image.

14. The method according to claim 1, further comprising:
transmitting, by the testing apparatus, third prompt information for prompting a subject to adjust a center of a pupil of an eye to be tested to be aligned with an imaging center point after receiving a start test instruction transmitted from a controller, wherein the center point appears in a visual field of the head-mounted testing equipment and belongs to a pre-displayed reference element for assisting in acquiring the movement trajectory of the pupil in the electronic equipment.

15. The method of claim 14, further comprising:
acquiring, by the testing apparatus, an identity label of a subject, and receiving the start test instruction after acquiring the identity label.

16. The method of claim 14, further comprising:
acquiring, by the testing apparatus, an identity label of a subject according to iris information of a current eye to be tested of the subject, and then receiving the start test instruction after acquiring the identity label.

17. The method of claim 1, further comprising:
upon receiving, by the testing apparatus of the electronic equipment, a start instruction triggered by a user, displaying a predicted image of the eye to be tested, and inserting the electronic equipment into the head-mounted testing equipment to display the image information on the screen of the electronic equipment within the visual field of the head-mounted testing equipment;
when the visual field of the head-mounted testing equipment is arranged in front of an eye of a subject, adjusting a focal length button of the head-mounted testing equipment such that the image information seen by the pupil of the eye to be tested of the subject is clearest; and
starting a testing process after the controller transmits a start test instruction upon receiving the start instruction triggered by the subject.

18. A system for performing a visual field test, comprising:
electronic equipment comprising a testing apparatus;
head-mounted testing equipment; and
an eye movement tracking system, wherein the electronic equipment is independent from the head-mounted testing equipment, wherein the electronic equipment is located in the head-mounted testing equipment during the visual field test, wherein the electronic equipment is communicatively connected to a controller associated with the head-mounted testing equipment to receive a signal transmitted when a subject triggers the controller, and wherein the testing apparatus of the electronic equipment is configured to:
transmit a start notification for starting monitoring of a movement trajectory of a pupil of an eye to be tested to an eye movement tracking system after receiving a start test instruction transmitted from the controller;
display image information on a screen of the electronic equipment within a visual field of the head-mounted testing equipment receive movement state information of the pupil transmitted from the eye movement tracking system; and
determine the movement trajectory of the pupil according to the movement state information.

19. The system of claim 18, wherein the electronic equipment further comprises the eye movement tracking system.

20. Electronic equipment, comprising:
a processor; and
a memory storing a plurality of instructions that, when executed by the processor, cause the processor to:
upon receiving a start test instruction transmitted from a controller, transmit, to an eye movement tracking system, a start notification for starting monitoring of a movement trajectory of a pupil of a current eye to be tested in a visual field test, wherein the controller is a component that is associated with head-mounted testing equipment and communicatively connected to testing apparatus of the electronic equipment;

display image information on a screen of the electronic equipment within a visual field of head-mounted testing equipment;

receive movement state information of the pupil transmitted from the eye movement tracking system; and determine the movement trajectory of the pupil according to the movement state information of the pupil, wherein the electronic equipment is independent from the head-mounted testing equipment, and wherein the electronic equipment is located within the head-mounted testing equipment during the visual field test.

* * * * *